Oct. 29, 1957 R. BAERMAN ET AL Plant Pat. 1,655
GLADIOLUS PLANT
Filed Sept. 12, 1956
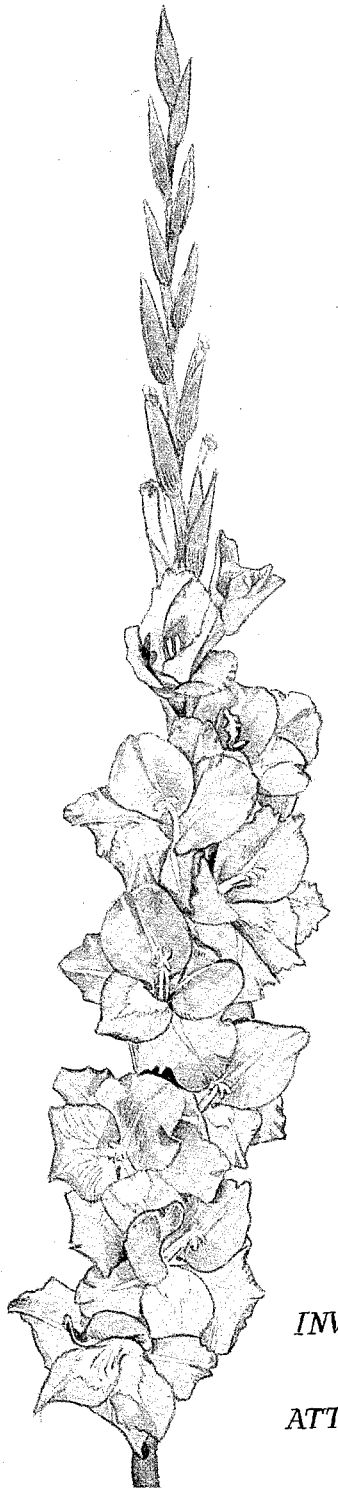
INVENTORS
RALPH BAERMAN
CARL H. FISCHER
ATTORNEY
Lamont Johnston United States Patent Office Plant Pat. 1,655
Patented Oct. 29, 1957

1,655

GLADIOLUS PLANT

Ralph Baerman, Arlington, Va., and Carl Fischer, St. Charles, Minn., assignors to Selected Glads, Inc., Nashville, Tenn., a corporation of Tennessee Application September 12, 1956, Serial No. 609,514

1 Claim. (Cl. 47—60)

Our present invention relates to a new and improved variety of gladiolus plant, and is notable for the size and quantity of bloom, delicate and distinctive coloring, heavy substance of petals, and apparent freedom from disease. It is a variety of unusual health and vigor.

This new variety is the result of a cross between the varieties Beauty's Blush (unpatented) as the seed parent, and a purple seedling (unpatented) as the pollen parent, this seedling having been derived from Gloaming (unpatented) and Rose O'Day (unpatented). It was produced by hand pollination done by the first-named inventor in a rented garden near his home when living at Suitland, Maryland, and it exhibits the traits of both parents. It was asexually reproduced in Minnesota by the second-named inventor by natural increase from cormels. Through several generations, its characteristics have proved to be permanently fixed.

The illustration forming a part of this application shows a spike of the bloom of this new variety in approximately its true natural coloring.

In the following detailed description, color plate references are to Ridgway's Color Standards and Nomenclature, edition of 1812. Where there are other references to color, the ordinary dictionary meaning of the term is intended.

*The plant*

Growth: Very vigorous, averaging 60 inches in height under good growing conditions. It is a very good propagator.

Blooming habit: Each spike opens 7 to 9 florets at one time, spikes totalling 20 to 22 flowers and buds. In addition to the blooms that are open, 5 buds will be showing color. The variety is an early midseason bloomer, coming into flower from No. 1 bulbs in 75 to 80 days, depending on the season.

Disease resistance: Very resistant to diseases, such as Fusarium wilt, Sclerotinia dry rot, and Botrytis, to which gladiolus varieties are subject, even when grown alongside another variety which is disease-infested. This was observed when this variety was grown as a seedling under irrigation in a black loam soil in the vicinity of St. Charles, Minnesota, under the natural conditions provided by the climate of that area. At the end of the season, other varieties and seedlings would succumb to the various diseases, whereas this variety remained hale and hearty.

Stems: Straight, wiry and whip-like; approximately Parrot Green (Plate VI). Diameter at base averages 1 to 1¼ inches.

Foliage: Spinach Green (Plate V). Averages 2½ inches wide and 38 inches high, remaining green until digging time.

Corms: Healthy, smooth and with a normal husk. Average size from mature plants is 3 inches in diameter.

Spike: Long and slender. Has 20 to 22 buds and flowers, of which 3 to 5 open the first day, following which 7 to 9 are open at one time until all have bloomed.

*The flower*

Bud:

*Size.*—Buds beginning to open are 3 inches long.

*Color.*—Rhodamine Purple (Plate XII).

*Opening.*—7 to 9 buds show color at one time, with 3 to 5 opening the first day.

Flower:

*Arrangement.*—Flowers are closely and evenly spaced on the spike and all face in about the same direction.

*Size.*—Fully opened floret measures 4½ to 5 inches in diameter.

*Form.*—Wide-open; regular; with six petals, the three upper ones larger than the others.

*Keeping qualities.*—Flowers keep and ship very well.

Petals:

*Shape.*—Upper petals are unusually wide. There is a light ruffling or wrinkling at the extreme edge, extending inward ¼ to ½ inch.

*Size.*—The longer petals are 2½ inches in length and 1¾ inches wide. The throat petals are 1¾ inches long and 1¼ inches wide.

*Aspect.*—Substance is heavy; surface texture smooth and waxy.

*Fragrance.*—None.

*Color.*—The predominating color is Rhodamine Purple (Plate XII). It is a self-color throughout, except for Light Mallow Purple midribs (Plate XII) and except for a sharp Ivory White throat blotch, 1 inch across, covering the inner half, usually of one throat petal, but occasionally of two.

Reproductive organs: The stamens are of Amparo Purple color and are ⅝ inch in length.

Having thus disclosed our invention, we claim:

The new and distinct variety of gladiolus plant substantially as herein shown and described, characterized particularly by its unusual health and vigor; its very good propagation; its long and slender spikes; the close and even spacing of the flowers on the spike with all facing in about the same direction; its large, healthy corms; the large number of florets showing color at one time; and the Rhodamine Purple color of its flower, with Light Mallow Purple midribs and a distinguishing sharp Ivory White throat blotch covering the inner half of one or two throat petals.

No references cited.